United States Patent
Li et al.

(10) Patent No.: US 9,314,792 B2
(45) Date of Patent: Apr. 19, 2016

(54) DEVICE FOR COLLECTING ORAL FLUID SAMPLES AND THE LIKE

(71) Applicant: AVIOQ, INC., Research Triangle Park, NC (US)

(72) Inventors: Xingxiang Li, Cary, NC (US); Chamroen Chetty, Durham, NC (US); Krista Reddington, Hillsborough, NC (US); Mike Cronin, Raleigh, NC (US)

(73) Assignee: Avioq, Inc., Research Triangle Park, NC (US)

( * ) Notice: Subject to any disclaimer, the term of this patent is extended or adjusted under 35 U.S.C. 154(b) by 0 days.

(21) Appl. No.: 13/889,009

(22) Filed: May 7, 2013

(65) Prior Publication Data

US 2013/0302219 A1    Nov. 14, 2013

Related U.S. Application Data

(60) Provisional application No. 61/643,962, filed on May 8, 2012.

(51) Int. Cl.
*B01L 3/00* (2006.01)
*A61B 10/00* (2006.01)
*G01N 1/02* (2006.01)

(52) U.S. Cl.
CPC ......... *B01L 3/50825* (2013.01); *A61B 10/0045* (2013.01); *B01L 3/5029* (2013.01); *A61B 10/0051* (2013.01); *B01L 2300/047* (2013.01); *B01L 2400/0481* (2013.01); *G01N 2001/028* (2013.01)

(58) Field of Classification Search
None
See application file for complete search history.

(56) References Cited

U.S. PATENT DOCUMENTS

| 4,184,483 A * | 1/1980 | Greenspan ......... A61B 10/0096 435/304.2 |
| 7,300,632 B2 * | 11/2007 | Sugiyama et al. ............ 422/547 |
| 2007/0148724 A1 * | 6/2007 | Salter et al. ..................... 435/32 |
| 2008/0260581 A1 * | 10/2008 | Rosman et al. ............... 422/68.1 |
| 2009/0030342 A1 * | 1/2009 | Flanigan et al. .............. 600/572 |
| 2009/0171245 A1 * | 7/2009 | Uhl et al. ....................... 600/572 |

FOREIGN PATENT DOCUMENTS

WO    WO 2010020043 A1 *    2/2010    ............ B01L 3/5029

* cited by examiner

*Primary Examiner* — Jill Warden
*Assistant Examiner* — Benjamin Whatley
(74) *Attorney, Agent, or Firm* — Olive Law Group, PLLC

(57) ABSTRACT

Devices for collection and elution of oral fluid samples and the like enable collection and elution of samples by using a handle in the form of a rod having a collection pad thereon which is inserted into a collection tube. The collection tube has an adaptor with a narrowed portion associated therewith for squeezing the pad to wring a sample therefrom. In an alternative embodiment, the collection tube has a narrowed portion that squeezes the pad as the pad is inserted there though. Caps are provided to 1) support the rod in an assembly with the adaptor and collection tube to form an assembled sample collection device and 2) to close the collection tube after the handle and pad are removed from the collection tube subsequent to depositing the sample elution solution therein. The eluted sample can be used for detection of an analyte.

8 Claims, 4 Drawing Sheets

A Cross-sectional Diagram for an Assembled Sample Collection Device. The device is composed of a cap 1, an adaptor 2 with narrow inner passage 3, a handle 4, a sample collection tube 5 and a collection pad wrapped around the bottom end of the handle 6.

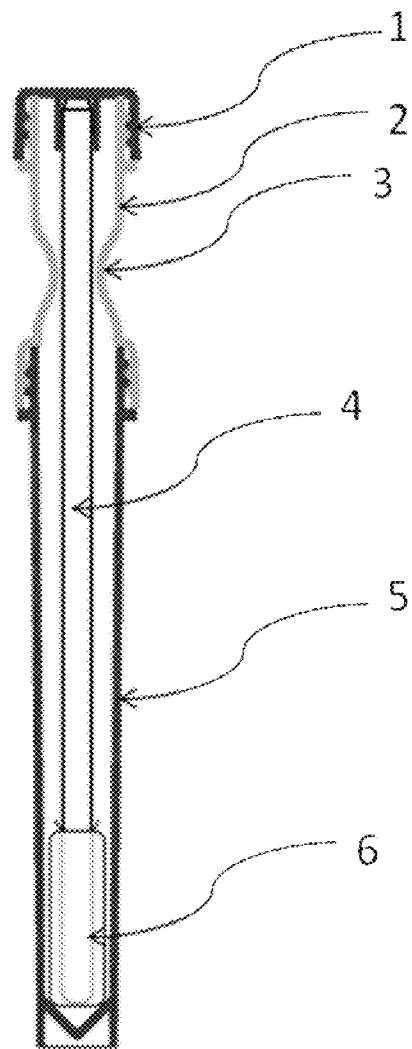
Fig 1: A Cross-sectional Diagram for an Assembled Sample Collection Device. The device is composed of a cap 1, an adaptor 2 with narrow inner passage 3, a handle 4, a sample collection tube 5 and a collection pad wrapped around the bottom end of the handle 6.

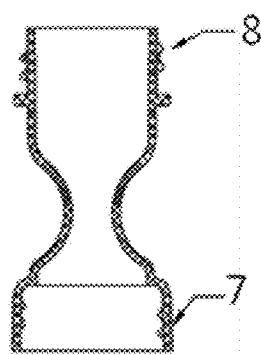
Fig 2: A Cross-sectional Diagram for an Adaptor in one Embodiment. The adaptor has a narrow passage, female threads at one end 7 and male threads at the other end 8.

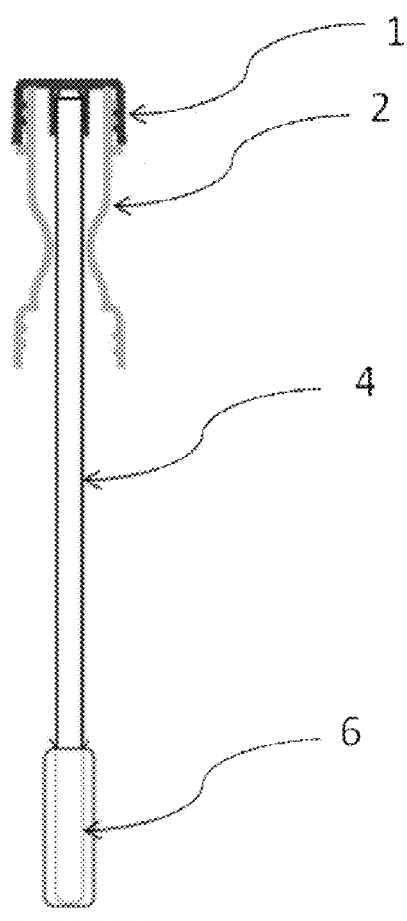
Fig 3: A Cross-sectional Diagram of a Sample Collection Unit. The sample collection unit is composed of a cap 1, an adaptor 2, and a handle 4 mounted to the cap 1 on one end and wrapped with the collection pad 6.

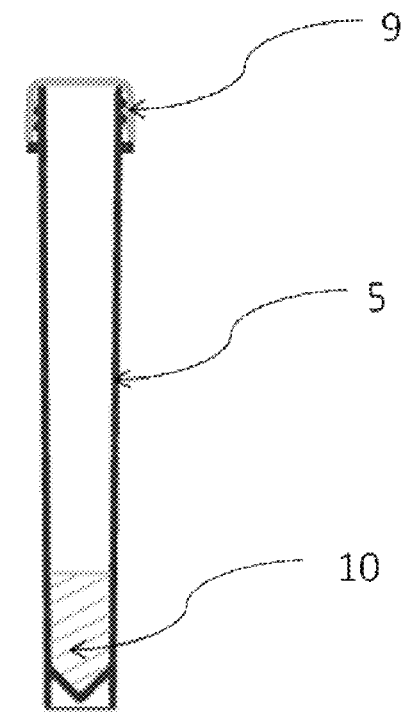
Fig 4: A Cross-sectional Diagram Showing a Sample Collection Tube Filled with Sample Elution Solution. The sample collection tube is composed of a cap 9, the collection tube 5 and sample elution solution 10.

US 9,314,792 B2

DEVICE FOR COLLECTING ORAL FLUID SAMPLES AND THE LIKE

CROSS-REFERENCE TO RELATED APPLICATION

This application claims priority to U.S. Provisional Application No. 61/643,962, filed May 8, 2012. The entire disclosure of the prior application is considered to be part of the disclosure of the instant application and is thereby incorporated by reference.

TECHNICAL FIELD

The present invention relates to devices for collection and elution of biological samples, including oral fluid samples. The collected sample can be used for detection of an analyte.

BACKGROUND OF THE INVENTION

Fluid and cellular samples collected from the buccal cavity contain a number of analytes or markers that are indicative of diseases or other health conditions of the sample donors. These samples, which include saliva and oral mucosal transudate (OMT), are referred to as oral fluid samples in this application. The analytes contained in the oral fluid samples include biomarkers, such as specific antibodies to, and antigens from, pathogens, chemical markers such as cocaine and other drug abuse markers, and genetic markers. Because of the noninvasive nature of collecting oral fluid samples, these samples are preferred, where appropriate, to use for the analyte detection.

One commonly used method for collecting an oral fluid sample is the use of a collection pad such as a sponge, which is connected to a handle. The collection pad absorbs the oral fluid while its surface can be used to collect epithelial cells by rubbing against the oral mucosa, including the surface of the gum. To collect an oral sample, one can rub the pad against the surface of gum and place the collection pad inside the buccal cavity. The collection pad now contains both epithelial cells and the saliva.

There are three general methods for recovering the sample from the collection pad. One method involves inserting the collection pad into an elution buffer and, after equilibration with the buffer, removing the collection pad. The second method involves wringing the collection pad by pressing the pad against a surface. For example, U.S. Pat. No. 5,339,829 describes a device which consists of a plunger attached with a collection pad and a syringe barrel, which is used to wring the saliva out of the pad. Yet another method for recovering the oral fluid sample from the collection pad is centrifugation.

There are a number of shortcomings for these methods of oral fluid sample recovery. While direct removal of the collection pad from a sample elution solution is simple, it considerably reduces the recovered sample amount as the collection pad itself can absorb a considerable amount of the sample when it is removed, leading to insufficient amounts of sample or a highly diluted sample for analyte detection. Wringing the sample out of the collection pad is difficult to perform and recovery efficiency is often inconsistent. Centrifugation involves the use of a centrifuge, which is not always available, particularly at point-of-care settings.

Similar problems exist for collecting other biological samples. These samples include, but are not limited to, vaginal specimens, wound specimens, and environmental samples.

We have now invented a simple device, which allows efficient extraction of the fluidic and adsorbed materials from the sample collection pad by simply pulling the collection pad through a narrow passage, resulting in the recovery of a considerable amount of the samples without using centrifugation. The method of collecting and recovering a sample described in the present invention is simple and user friendly.

SUMMARY OF THE INVENTION

The sample collection device in the present invention consists of three basic parts, (a) a handle mounted onto a cap at one of its ends and wrapped with a collection pad at the other end, (b) an adaptor with a narrow passage, which allows the collection pad to be pulled through the passage thereby wringing out the sample, and (c) a sample collection tube for sample elution and collection. The narrow passage in the adaptor is slightly larger than the handle, thereby allowing the collection pad to be pulled through and wringing the fluidic sample and/or adsorbed materials out of the collection pad into the sample collection tube. In order for the absorbed sample to be efficiently wringed out, the handle is made of a rod, which is ideally rounded with smooth surfaces and has an outer diameter slightly smaller than the inner diameter of the narrow passage of the adaptor.

In a preferred embodiment, the handle is mounted to the cap via the end without the wrapped collection pad; the adaptor contains screw threads at both ends, which allows the adaptor to be engaged with the cap and/or the sample collection tube. In this preferred design, the handle is mounted to the cap at one end and wrapped with the collection pad at the other end and can be attached to the adaptor to assemble into a sample collection unit, which is normally sterilized and packaged into a single unit. When necessary, the sample collection tube is filled with an appropriate amount of sample elution solution to elute the sample.

Thus, sample collection and elution essentially involves six steps: 1) collection of a sample using the sample collection unit by inserting the collection pad into a liquid sample or by rubbing against the collection site to collect a non-liquid sample, 2) insertion of the handle with the collection pad into the sample collection tube and screwing the adaptor to engage the entire sample collection unit with the sample collection tube, 3) unscrew the cap mounted with the handle, 4) rotate the handle, if necessary, to fully submerge the collection pad in the sample elution solution and to allow adequate mixing of the adsorbed sample with the elution solution, 5) pull out the handle along with the collection pad through the narrow passage of the adaptor, thereby wringing out the fluidic and/or adsorbed materials from the pad into the sample collection tube and 6) unscrew the adaptor and screw a cap on the collection tube and store the sample properly.

DESCRIPTION OF THE DRAWINGS

FIG. 1: A side elevation of a preferred embodiment of an assembled sample collection device according to the invention.

FIG. 2: A side elevation of an adaptor shown in FIG. 1.

FIG. 3: A side elevation of sample collection unit portion of FIG. 1.

FIG. 4: A side elevation of a sample collection tube shown in FIG. 1.

DETAILED DESCRIPTION OF THE INVENTION

FIG. 1 illustrates an assembled sample collection device in one embodiment. There are four basic components: a) a cap 1, b) an adaptor 2 with a narrow passage 3, c) a handle 4 mounted to the cap 1 at one end and wrapped with a collection pad 6 at another end, and d) a sample collection tube 5. These parts can be separated into two units, a sample collection unit (FIG. 2) comprising a cap 1, an adaptor 2 and a handle 4, and a sample collection tube unit (FIG. 4) comprising a tube 5, a cap 9 and sample elution solution 10.

In a preferred embodiment, the cap 1 has female screw threads compatible with the male screw threads in the adaptor 2 and the male screw threads in sample collection tube 5. The inner diameter of the narrow passage 3 of the adaptor 2 is slightly larger than that of the handle 4. An appropriate inner diameter of the narrow passage allows the collection pad 6 to pass through and wring out the sample from the collection pad 6. The inner diameter of the narrow passage is slightly larger than the outer diameter of the handle by about 0.5 mm to about 5 mm, ideally by about 1 to 1.5 mm. It is understood that appropriate inner diameter of the narrow passage of the adaptor may need to be experimentally determined, depending on the outer diameter of the handle portion when wrapped with the collection pad 6 and the thickness of the collection pad.

In certain embodiment, as illustrated in FIG. 2, the adaptor 2 has three basic features: a) female screw threads 7 on one end, which are compatible with the male screw threads on the sample collection tube 5, b) male screw threads 8 on the other end, which are compatible with the female screw threads of the cap 1 or cap 9, and c) a narrow passage 3 in the middle.

Cap 1 of FIGS. 1 and 3 and cap 9 of FIG. 4 are identical except that cap 1 is mounted with the handle 4, which is wrapped with the collection pad 6 on the other end. In a preferred embodiment, the handle 4 is securely mounted onto cap 1 as is shown in FIGS. 1 and 3. In certain preferred embodiment, the handle 4 cannot be disengaged from cap 1 without leaving a visible mark to prevent intentional or accidental mixing up of samples.

The collection pad 6 is normally made of a textured material, which has high sample collection capacity. In certain preferred embodiments, the collection pad has a highly porous texture, which enhances its liquid collection capability. Appropriate materials of the collection pad include, but are not limited to, cellulose, polyurethane, polyester, polystyrene, and rayon.

The collection pad 6 is securely wrapped around one end of the handle 4. A preferred handle is a rounded rod with minimal sample adsorption capability and with a smooth surface. The handle can be solid or hollow. In certain embodiments, the portion of the handle, which is in contact with the collection pad 6, is slightly larger than the other portion, allowing a larger contact area for the collection pad. An example of the handle 4 is a rounded polypropylene plastic rod.

The cap 1, adaptor 2, and handle 4 with collection pad 6 can be assembled into a single unit, the sample collection unit, as illustrated in FIG. 3. The sample collection unit is used for sample collection. As the sample collection unit is in contact with the site of sample collection, it is normally sterilized and sealed in a microorganism-impermeable package.

The mouth of sample collection tube 5 contains screw threads that are compatible with those in cap 1 and at one end of the adaptor 2. When assembled, the collection pad 6 can reach the bottom of the sample collection tube, thereby allowing the collection pad 6 to be submerged in sample elution solution, as illustrated in FIG. 1. In a preferred embodiment, the inner diameter of the bottom portion of the sample collection tube is slightly larger than the outer diameter of the collection pad 6 wrapped around the handle. The smaller diameter at the tube bottom reduces the amount of sample elution solution, thereby preventing the samples from being overly diluted. The tube wall in the bottom can be made thicker to make the inner diameter smaller than that for the upper portion to maintain the same outer diameter of the test tube. Alternatively, the outer diameter of the bottom portion can be made smaller to maintain similar thickness of the tube wall throughout the tube.

The collection tube 5 is normally filled with a sample elution solution, capped and packaged as a separate unit as shown in FIG. 4. A variety of sample elution solution formulations are available in the literature. Those skilled in the art will have the ability to select an appropriate buffer solution for the present device and for the analyte(s) to be detected. For example, a typical sample elution solution contains a buffering agent such as phosphate salts, a salt such as sodium chloride, a protease inhibitor such as phenylmethanesulfonylfluoride (PMSF), a preservative such as sodium azide, and a detergent such as Triton X-100. The amount of sample elution solution filled in the collection tube is from about 0.25 mL to about 5 mL/tube, preferably about 1 mL/tube.

The present sample collection device can be assembled into a kit, which contains two parts: the sample collection unit as illustrated in FIG. 3 and sample collection tube with sample elution solution as illustrated in FIG. 4.

Example 1 describes a procedure for collecting an oral fluid sample using the device. The procedure includes a) insertion of the sample collection unit (FIG. 3) into the mouth, b) rubbing the collection pad 6 against the gum area, c) rotating the pad and rubbing a different gum area, d) placing the collection pad under the tongue for an appropriate period of time to be determined experimentally to allow adsorption of saliva, e) removing the sample collection unit from the mouth, f) placing it into the sample collection tube, and g) tightly screwing the adaptor 2 to the sample collection tube. The collected sample can be eluted and retained in the test tube at the site of collection or at the site of testing.

To elute and recover the collected sample, the cap 1 to which the handle is attached (FIG. 1) is unscrewed. The collection pad 6 is pulled through the narrow passage of the adaptor 2. The adaptor is unscrewed from the sample collection tube, which now contains the collected sample. The sample collection tube is then capped and stored under appropriate conditions. The used sample collection unit can be discarded or stored in an appropriate container for long-term storage.

It is understood that the present sample collection device can be used to collect samples from different sources, including, but are not limited to, the oral cavity for collection of oral fluid samples, vagina for collection of vaginal samples, wound for collecting wound samples, and environmental surface for collecting environmental samples. The sample source may include liquid solutions.

It is understood that a number of modifications and changes can be made to the preferred embodiment without changing the scope of the present invention. For example, the sample collection tube can be constructed to contain a narrow passage to replace the adaptor, in which case the adsorbent pad goes through the narrow passage twice (in and out) to extract the adsorbed sample.

The entire disclosures of all applications, patents and publications, cited herein and of corresponding application No. 61/643,962 US filed May 8, 2012 are incorporated by reference herein.

EXAMPLE 1

A Procedure for Collecting an Oral Fluid Sample Using the Collection Device

The following is a procedure for collecting an oral fluid sample using the collection device described in the present invention. According to the present procedure, both oral fluid sample and cellular sample from the gum tissue may be collected.

a. Insert the collection pad in the sample collection unit (refer to FIG. 3) into the mouth,
b. Rub the collection pad 6 against the gum area,
c. Rotate the pad and rub a different gum area,
d. Place the collection pad under the tongue for an appropriate period of time to be determined experimentally,
e. Remove the sample collection unit from the mouth,
f. Place it into the sample collection tube,
g. Tightly screw the adaptor 2 to the sample collection tube.
h. Elute and recover the collected sample at the site of collection or at the site of testing as follows:
  1) Unscrew cap 1 to which the handle is attached (refer to FIG. 1)
  2) Rotate the handle to fully submerge the collection pad in the sample elution solution and to allow adequate mixing of the fluidic sample and/or adsorbed materials with the elution solution,
  3) Slowly pull the collection pad 6 through the narrow passage 3 of the adaptor 2.
  4) Unscrew the adaptor from the sample collection tube, which now contains the collected sample.
  5) Cap the sample collection tube and store the tube under appropriate conditions. The used sample collection unit can be discarded or stored in an appropriate container for long-term storage.

EXAMPLE 2

Detection of Human Immunoglobulin G in Oral Fluid Samples Collected with the Sample Collection Device In the present example, a sample collection device described in the present invention was used to collect and recover oral fluid samples from 25 individuals according to the procedure described in Example 1. The collected oral fluid samples were tested to estimate the human immunoglobulin G (Ig G) concentration in the sample using a commercially available kit from Thermo Scientific (Easy-Titer® Human IgG (H+L) Assay Kit, Product Number 23310) and whole human Ig G, also from Fisher Scientific (Product Number 31154), as the standard for quantitation.

The samples were coded and blinded prior to testing. Each sample was tested in duplicate according to the procedure provided by the test kit manufacturer. After completion of the testing, the test samples were uncoded. The sample number, age of the sample donor, sex and average concentrations of Ig G are summarized in Table 1. Among this sample group, the average Ig G concentration ranged from 20.7 micrograms per milliliter to 140.7 micrograms per milliliter. The study described in this Example showed that the sample collection device described in the present invention could be used to collect oral fluid samples, which contain Ig G analytes.

TABLE 1

Detection of Human Ig G in Collected Oral Fluid Samples

| Sample Number | Sex | Age | Average Ig G Content (Micrograms/milliliter) |
| --- | --- | --- | --- |
| 1 | M | 62 | 28.4 |
| 2 | M | 55 | 27.8 |
| 3 | M | 60 | 123.5 |
| 4 | M | 49 | 26.4 |

TABLE 1-continued

Detection of Human Ig G in Collected Oral Fluid Samples

| Sample Number | Sex | Age | Average Ig G Content (Micrograms/milliliter) |
| --- | --- | --- | --- |
| 5 | M | 38 | 53.2 |
| 6 | M | 57 | 25.4 |
| 7 | M | 63 | 28.7 |
| 8 | F | 58 | 41.9 |
| 9 | F | 38 | 40.2 |
| 10 | M | 20 | 33.3 |
| 11 | M | 63 | 25.8 |
| 12 | F | 48 | 46.9 |
| 13 | F | 53 | 34.1 |
| 14 | F | 62 | 55.7 |
| 15 | F | 60 | 54.5 |
| 16 | M | 36 | 40.4 |
| 17 | F | 38 | 20.7 |
| 18 | M | 35 | 41.3 |
| 19 | M | 56 | 140.7 |
| 20 | M | 48 | 61.2 |
| 21 | M | 58 | 41.2 |
| 22 | F | 45 | 54.8 |
| 23 | F | 34 | 44.0 |
| 24 | F | 27 | 27.8 |
| 25 | F | 46 | 47.3 |

EXAMPLE 3

Detection of Continine in Oral Fluid Samples Collected with the Sample Collection Device Study described in this example was designed to discern smokers from non-smokers by testing cotinine in oral fluid samples collected with the sample collection device described in the present invention. Cotinine is an alkaloid of tobacco and a metabolite of nicotine. Presence of cotinine in the collected sample is indicative of smoking of the sample donor.

Oral fluid samples from 15 individuals were collected and recovered using the sample collection device described in the instant invention according to a procedure described in Example 1. Each collected sample was tested using a cotinine test that is commercially available (OraSure Technologies). The smoking status was correctly identified for all 15 samples, which include samples from 8 smokers and 7 non-smokers (Table 2). These results showed that the oral fluid samples collected with the sample collection device described in the present invention could be used for detection of cotinine.

TABLE 2

Detection of Cotinine in Collected Oral Fluid Samples

| Sample | | | Cotinine Test Results | | |
| --- | --- | --- | --- | --- | --- |
| Number | ID | Number of Cigarettes Smoked per day | Smoking Status | OD Reading | Signal to Cutoff Ratio* | Cotinine Positive/ Negative |
| 1 | SMO101 | 15 | Smoker | 0.315 | 0.897 | Positive |
| 2 | NO104 | 0 | Nonsmoker | 1.304 | 3.715 | Negative |
| 3 | SMO106 | 10 | Smoker | 0.181 | 0.516 | Positive |
| 4 | SMO102 | 10 | Smoker | 0.100 | 0.285 | Positive |
| 5 | NO105 | 0 | Nonsmoker | 1.367 | 3.895 | Negative |
| 6 | SMO107 | 20 | Smoker | 0.060 | 0.171 | Positive |
| 7 | NO101 | 0 | Nonsmoker | 1.570 | 4.473 | Negative |
| 8 | NO106 | 0 | Nonsmoker | 1.224 | 3.487 | Negative |
| 9 | SMO108 | 10 | Smoker | 0.129 | 0.368 | Positive |
| 10 | NO102 | 0 | Nonsmoker | 1.351 | 3.849 | Negative |

TABLE 2-continued

Detection of Cotinine in Collected Oral Fluid Samples

| | Sample | | | Cotinine Test Results | | |
|---|---|---|---|---|---|---|
| Number | ID | Number of Cigarettes Smoked per day | Smoking Status | OD Reading | Signal to Cutoff Ratio* | Cotinine Positive/ Negative |
| 11 | NO107 | 0 | Nonsmoker | 1.528 | 4.353 | Negative |
| 12 | NO103 | 0 | Nonsmoker | 1.263 | 3.598 | Negative |
| 13 | SMO104 | 15 | Smoker | 0.233 | 0.664 | Positive |
| 14 | SMO103 | 5 | Smoker | 0.149 | 0.425 | Positive |
| 15 | SMO105 | 6 | Smoker | 0.177 | 0.504 | Positive |

*Presence of cotinine or smoking is indicated when the signal to cutoff ratio is equal to or less than 1.0.

We claim:

1. A sample collection device comprising:
   (a) a screw cap comprising screw threads;
   (b) a handle comprising a first end and a second end wherein the second end is removably attached to said cap;
   (c) a collection pad affixed to the first end of said handle;
   (d) a sample collection tube having an open end and a closed end with screw threads at the open end adapted to engage the screw threads of said cap or the screw threads of an adaptor, said sample collection tube having a diameter sufficient to receive said handle and said collection pad;
   (e) an adaptor comprising a first end, a second end and a narrow passage between the first end and the second end, wherein the first end comprises a first set of screw threads adapted to engage the screw threads on the open end of the sample collection tube and the second end comprises a second set of screw threads adapted to engage the screw threads of said cap, and wherein said handle and collection pad extend into the collection tube and pass through the narrow passage, the narrow passage having an inner diameter which
   (1) is slightly greater than an outer dimension of the handle to allow the handle to pass through the narrow passage; and
   (2) is smaller than an outer dimension of said collection pad, so as to squeeze the collection pad when passed through the narrow passage.

2. The device of claim 1, wherein said handle is a rounded rod.

3. The device of claim 1, wherein said collection pad is wrapped around the handle at the first end.

4. The device of claim 1, wherein said adaptor has male screw threads on one end and female screw threads on the other end.

5. The device of claim 1, wherein said sample collection tube comprises a collection tube cap and has male screw threads compatible with the collection tube cap.

6. The device of claim 1, wherein the bottom portion of said sample collection tube is smaller in inner diameter than that for the upper portion, thereby allowing the sample collection tube to accommodate a smaller collection pad and use less sample elution solution to avoid over dilution of the collected sample.

7. The device of claim 1, wherein said sample collection tube has rough inner surface against which the collection pad can be rubbed to facilitate elution of the sample from the collection pad.

8. The device of claim 1, wherein said cap, handle, collection pad and adaptor are assembled into a single sample collection unit.

* * * * *